(12) United States Patent
Picha et al.

(10) Patent No.: US 9,138,218 B2
(45) Date of Patent: Sep. 22, 2015

(54) TISSUE RETRACTOR STAY

(75) Inventors: George J. Picha, Brecksville, OH (US);
Matt Thompson, Broadview Heights, OH (US); Dawn Thompson, Broadview Heights, OH (US)

(73) Assignee: ABEON MEDICAL CORPORATION, Richfield, OH (US)

( * ) Notice: Subject to any disclaimer, the term of this patent is extended or adjusted under 35 U.S.C. 154(b) by 860 days.

(21) Appl. No.: 12/788,800

(22) Filed: May 27, 2010

(65) Prior Publication Data
US 2011/0295075 A1    Dec. 1, 2011

(51) Int. Cl.
*A61B 1/32* (2006.01)
*A61B 17/02* (2006.01)

(52) U.S. Cl.
CPC ............. *A61B 17/0293* (2013.01); *A61B 17/02* (2013.01); *A61B 2017/0287* (2013.01)

(58) Field of Classification Search
CPC ............... A61B 17/02; A61B 17/0293; A61B 2017/0287
USPC ............ 24/300–301; D24/135; 600/201, 206, 600/209, 210, 213, 215, 217, 227, 229
See application file for complete search history.

(56) References Cited

U.S. PATENT DOCUMENTS

| | | | |
|---|---|---|---|
| 3,762,401 A | 10/1973 | Tupper | |
| 4,430,991 A | 2/1984 | Darnell | |
| RE32,021 E | 11/1985 | Scott, Jr. | |
| 5,174,279 A * | 12/1992 | Cobo et al. | 600/206 |
| 5,514,076 A * | 5/1996 | Ley | 600/206 |
| 5,769,783 A | 6/1998 | Fowler | |
| 5,785,649 A * | 7/1998 | Fowler, Jr. | 600/233 |
| 5,899,853 A | 5/1999 | Fowler, Jr. | |
| 5,951,467 A | 9/1999 | Picha et al. | |
| 5,964,697 A | 10/1999 | Fowler, Jr. | |
| 5,964,698 A * | 10/1999 | Fowler | 600/217 |
| 6,077,221 A * | 6/2000 | Fowler, Jr. | 600/233 |
| 6,090,043 A * | 7/2000 | Austin et al. | 600/217 |
| 6,117,072 A * | 9/2000 | Fowler, Jr. | 600/217 |
| 6,190,312 B1 | 2/2001 | Fowler, Jr. | |
| 6,544,195 B2 * | 4/2003 | Wilson et al. | 600/564 |
| 2007/0156023 A1 | 7/2007 | Frasier et al. | |
| 2007/0232864 A1 * | 10/2007 | Sharp et al. | 600/227 |

OTHER PUBLICATIONS

International Search Report for PCT/US2010/036366; Feb. 10, 2011.

* cited by examiner

*Primary Examiner* — Larry E Waggle, Jr.
(74) *Attorney, Agent, or Firm* — Pearne & Gordon LLP (57) ABSTRACT

A handleless surgical stay includes an elastomeric band with a longitudinal body having a first end. The surgical stay further includes a tissue retention member including a tissue engaging portion and an anchor portion. The anchor portion is coupled to the first end of the elastomeric band such that the tissue engaging portion extends outwardly relative to the first end. Substantially all of the elastomeric band can be configured for engagement with a surgical retractor frame such that the stay does not include a handle.

19 Claims, 5 Drawing Sheets

TISSUE RETRACTOR STAY

CROSS-REFERENCE TO RELATED APPLICATIONS

Not Applicable.

FIELD OF THE INVENTION

The present invention relates generally to a surgical retractor stay, and more particularly, to a surgical retractor stay having an elastomeric band.

BACKGROUND OF THE INVENTION

It has proven to be desirable in many surgical procedures to provide structure to maintain a surgical incision in an open or exposed condition. Several tissue retraction systems have been developed over the years in response to the need for a means to maintain tissue out of the way of the surgeon. One such system includes a frame or support and a tissue-engaging portion.

Stays for use with such frames are known in the art and generally have a retention hook, a handle and a band. However, these stays suffer from one or more disadvantages. Elastomeric bands having a uniform diameter without hubs tend to easily deform and slip through the retractor frame notches, thereby allowing the incision to close. In addition, many of the prior art stays have handles and bands that contain openings and/or cavities in which blood and debris can collect. Such a stay is not autoclavable or reusable.

In addition, the rigid handle region of the traditional surgical stay acts as a lever arm, mechanically amplifying any forces outside the force vector of retraction. The lever arm force amplification increases the tissue stress and damage at the distal interface of the stay and the tissue. The profile of a rigid stay handle can impede visibility and fine surgical technique at the surgical site. For example, surgical sutures being applied to the surgical site will often catch on stay handles due to their heightened profile within the surgical site. Generally, an elastic stay can contour to the surgical site to reduce the overall profile of the retractor system's intrusion during surgery. However, a rigid handle portion is a region of the stay that does not interface with the tissue or with the retractor frame, thereby limiting the total retractive capacity of the stay. In relatively smaller surgeries, the frame can interface with the stay very near to the rigid handle.

BRIEF SUMMARY OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect of the present invention, a surgical stay comprises an elastomeric band with a longitudinal body having a first end. The surgical stay further comprises a tissue retention member including a tissue engaging portion and an anchor portion. The anchor portion is coupled to the first end of the elastomeric band such that the tissue engaging portion extends outwardly relative to the first end. Substantially all of the elastomeric band can be configured for engagement with a surgical retractor frame such that the stay does not include a handle.

In accordance with another aspect of the present invention, a surgical stay comprises an elastomeric band comprising a longitudinal body with a first end. The surgical stay further comprises a tissue retention member comprising a tissue engaging portion coupled to an anchor portion. The anchor portion is at least partially embedded within the first end of the elastomeric band such that the tissue engaging portion extends outwardly relative to the first end of the band. Substantially all of the elastomeric band can be configured for engagement with a surgical retractor frame such that the stay does not include a handle.

In accordance with another aspect of the present invention, a handleless surgical stay comprises an elastomeric band comprising a longitudinal body of a generally uniform cross-sectional dimension with a first end. The surgical stay further comprises a tissue retention member comprising a tissue engaging portion non-removably coupled to an anchor portion. The anchor portion has a cross-sectional dimension less than the cross-sectional dimension of the longitudinal body and is at least partially embedded within the first end of the elastomeric band such that the tissue engaging portion extends from the first end of the band. The elastomeric band is formed of a material that conforms to the anchor portion to thereby inhibit disconnection during use.

It is to be understood that both the foregoing general description and the following detailed description present example and explanatory embodiments of the invention, and are intended to provide an overview or framework for understanding the nature and character of the invention as it is claimed. The accompanying drawings are included to provide a further understanding of the invention and are incorporated into and constitute a part of this specification. The drawings illustrate various example embodiments of the invention, and together with the description, serve to explain the principles and operations of the invention.

BRIEF DESCRIPTION OF THE DRAWINGS

The foregoing and other aspects of the present invention will become apparent to those skilled in the art to which the present invention relates upon reading the following description with reference to the accompanying drawings, in which.

DESCRIPTION OF EXAMPLE EMBODIMENTS

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

Figure 1:
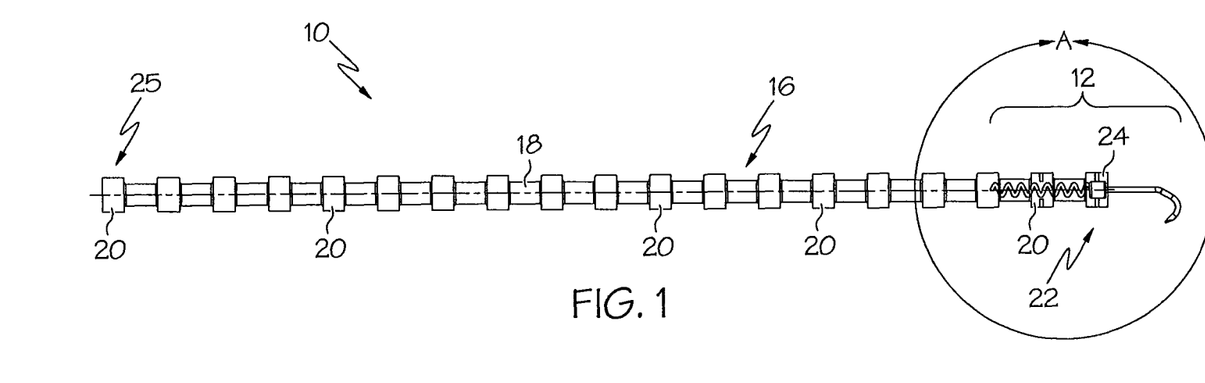
FIG. 1 is a side view of an example surgical retention stay.

Turning to the shown example of FIG. 1, a surgical retractor stay 10 according to a first embodiment of the present invention is illustrated. As will be described herein, the surgical stay 10 is an elastic handleless surgical stay. That is, substantially all of the stay 10 can be configured for engagement with a retractor frame 60, and/or surgical instruments, such that the stay 10 does not include a handle. Conventionally, a rigid handle region of the traditional surgical stay acts as a lever arm, mechanically amplifying any forces that increase the tissue stress and damage at the distal interface of the stay and the tissue. By contrast, an elastic handleless stay does not impart the tissue damage characteristics of a lever arm. Multi-planar elasticity will accommodate retractive forces outside the force vector of retraction without amplifying those forces and further damaging tissue. Tissue damage, especially to sub-dermal and delicate anatomical structures are be reduced, as are pathways of infection and cosmetic blemishes from said tissue damage.

The stay 10 includes a tissue retention member 12, and an elongated elastic member, or elastomeric band 16. As will be discussed in more detail below, substantially all of the elastomeric band 16 can be configured for engagement with a surgical retractor frame 60 (and/or surgical instruments) such that the stay 10 does not include a handle. For example, the elastomeric band 16 is configured for engagement with a notch 70 of the frame 60 (see FIG. 6), and the stay 10 is inhibited, such as prevented, from moving through the notch 70 (e.g., towards the surgical site 62) by mechanical interference. The band 16 has a longitudinal body 18 with a first end 22. In one example (see FIG. 5A), a plurality of hubs 20 can be disposed around the longitudinal body 18. The first end 22, where the tissue retention member 12 is located, can have one or more hubs disposed adjacent thereto. In one example, as shown, the first end 22 of the band 16 can be defined by at least one hub 24 such that said hub 24 terminates the first end 22 of the band 16. Though identified by a different reference number for clarity, it is understood that hub 24 can be identical to the other hubs 20. A distal end 25 of the band 16 can be located distal to the tissue retention member 12 and can also have one or more hubs 20 disposed adjacent thereto, such as defining and terminating said distal end 25. In another example (see FIG. 5D), the longitudinal body 18 can be relatively smooth without any hubs or the like.

The elastomeric band 16 is made from elastomeric material, such as silicone rubber, urethane polymers, etc. In one example, the band 16 is unitary and formed from a single element or multiple elements, such as a single elastic portion or multiple elastic portions, respectively. The band 16 preferably has a durometer/hardness within a range of about 40 D-60 D, though higher or lower durometer/hardness values are also contemplated. For example, various durometer values can provide various mechanical features, as shown in Table 1:

TABLE 1

| Durometer | Ultimate Elongation | Tensile Modulus (psi) | Tensile Strength (psi) |
| --- | --- | --- | --- |
| 40D | 650% | 230 | 1200 |
| 50D | 575% | 310 | 1250 |
| 60D | 450% | 330 | 1520 |

Figures 6, 7, 8:
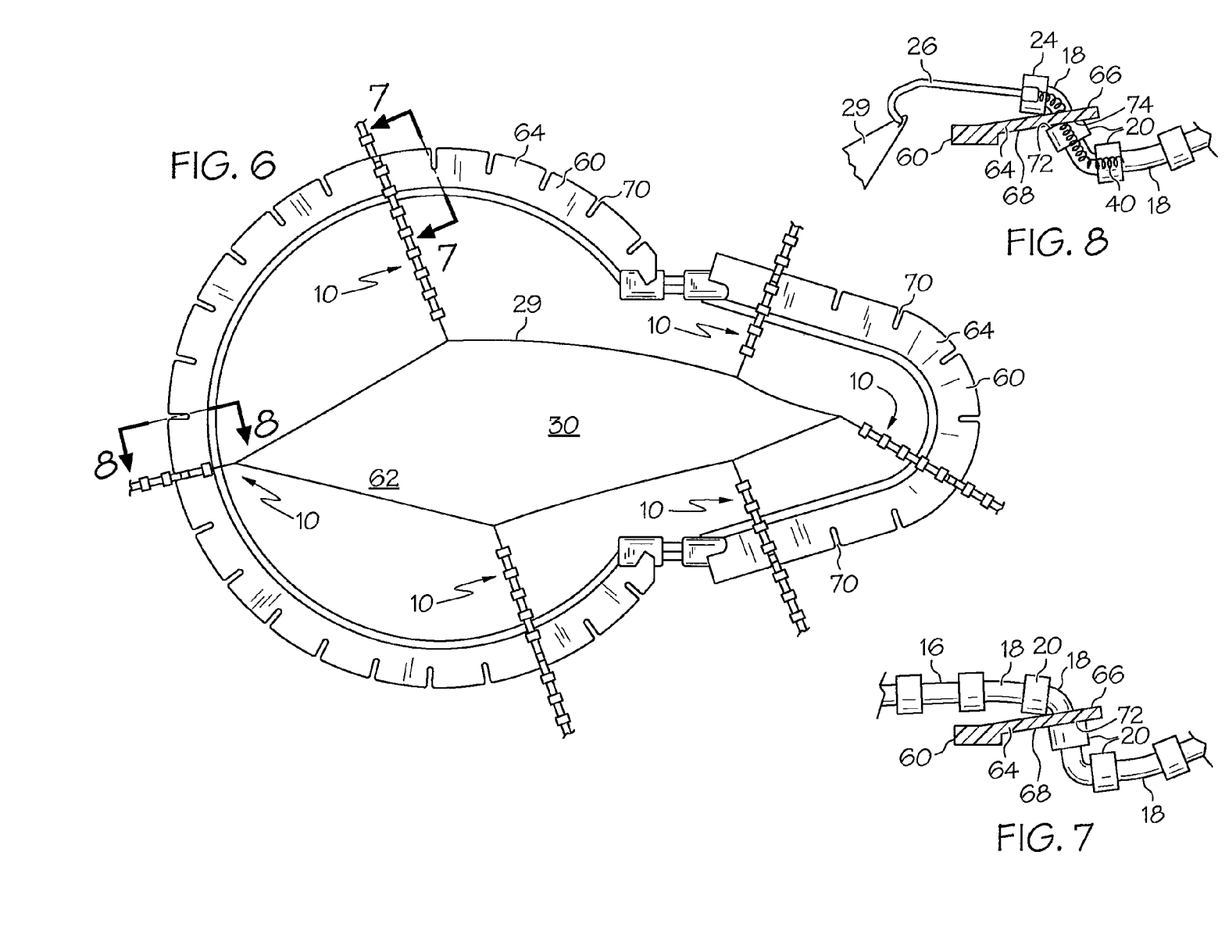
FIG. 6 is a schematic view of a series of surgical retractor stays in use with an example retractor frame.
FIG. 7 is a sectional view along line 7-7 of FIG. 6.
FIG. 8 is a sectional view along line 8-8 of FIG. 6.

As should be apparent, a relatively higher hardness will increase the engagement properties between the hubs 20, 24 and a surgical retractor frame 60. However, this can reduce the elastic qualities of the stay 10. This may not be desirable since a relatively less elastic stay 10 may lose characteristics desired by many surgeons, such as the ability of the tissue retention member 12 to move with the tissue 29 being retained as the surgical site 62 shifts during the operation to minimize tearing of the tissue 29 being retracted. The elastic characteristics also allow the stay 10 to be removed from the tissue 29 and/or the frame 60, and allow the band 16 to conveniently bend as best illustrated in FIGS. 6-8. As illustrated, multiple stays 10 can be used in concert with each other to hold the incision 30 open and thereby provide stable access to the incision 30.

Figure 2:
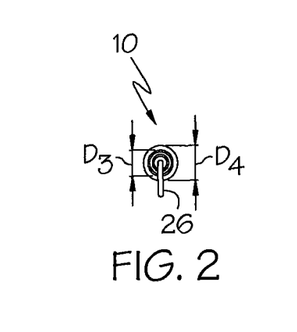
FIG. 2 is a front view of the surgical stay of FIG. 1.

With additional reference to FIGS. 1 and 2, a plurality of hubs 20 are disposed around the body 18 and are spaced apart along the length of the body 18. The hubs 20 extend radially from the body 18. In one example, the entire band 16 is integrally molded in a single molding process, including the hubs 20, 24 and the body 18. The hubs 20, 24 can be integrally molded with the body 18 to form the elastomeric band 16 as a unitary structure, such as a monolithic structure. Preferably, the band 16 is liquid injection molded. Each hub 20, 24 is provided with a frame engagement surface 72 at an end of the hub 20 facing the surgical site 62 for holding contact with the retractor frame 60. Even hub 24 at the first end 22 is provided with a frame engagement surface 72, and is fully functional for engagement with the frame 60. The frame engagement surface 72 can be an annular flat face disposed in a generally perpendicular relationship to the longitudinal axis of the body 18. For example, the band 16 can have an alternating series of cylindrical body portions and larger cylindrical hub 20 portions. The hubs 20, 24 can be provided with a broad, or planar, engagement surface 72 to contact the lower surface 68 of the flange 64 portion of the frame 60 surrounding the notch 70. See FIGS. 6-8. The engagement surface 72 is effective to distribute tension placed on the band away from the body 18 of the band 16 and thus away from the lower surface 68 area immediately adjacent the notch 70.

Still, the hubs 20, 24 can have various other geometries with various other engagement surface structure. For example, the hubs 20, 24 can have any of the geometries discussed in U.S. Pat. No. 6,090,043, the entire disclosure of which is incorporated herein by reference thereto. In various examples, any or all of the hubs 20, 24 can be spherical hubs, conical hubs, semi-spherical hubs, angled or beveled hubs with respect to the longitudinal axis of the band 16 (e.g., to match an angled flange 64 portion of the frame 60), and can have a bowl-shaped or concave engagement surface 72, or even have a molded fillet at an intersection of the body 18 and the engagement surface 72. In addition or alternatively, the body 18 and/or hubs 20, 24 can have various cross-sectional geometries, such as circular, oval, triangular and rectangular. The body 18 can also be relatively smooth without any hubs or the like. The described geometries of the body and hubs are not intended to limit the present invention.

Figure 3:
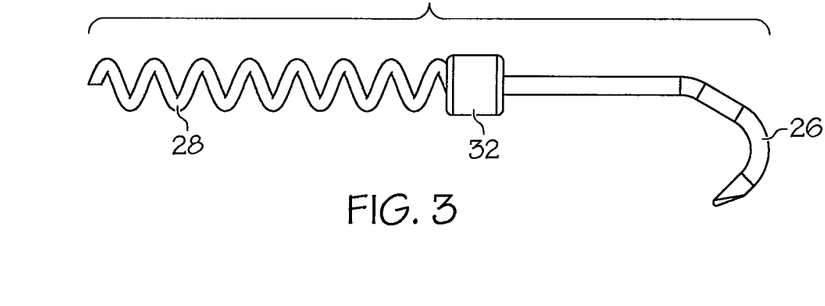
FIG. 3 is a side view of an example tissue retention member for use with the surgical stay of FIG. 1.
Figure 4A:
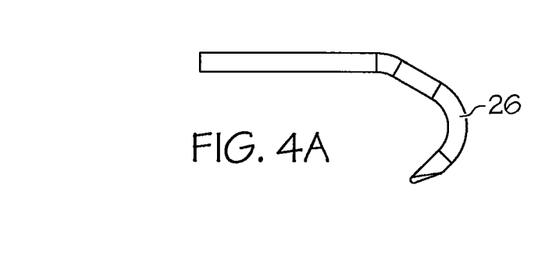
FIG. 4A is a side view of an example tissue-engaging portion of the tissue retention member of FIG. 3.

Turning back to FIGS. 3, 4A and 4B, the tissue retention member 12 generally has a tissue engaging portion 26, extending from the first end 22 of the band 16. The tissue retention member 12 is preferably made from a generally rigid material, such as metal (e.g., stainless steel, aluminum, titanium, etc.) or plastic. The material should be strong enough positively engage tissue 29 of the incision 30 and to withstand the tension forces applied to the surgical stay 10 when engaged with a retractor frame 60. The tissue retention member 12 can be made of a single material, or can be made of multiple materials. For example, the tissue-engaging portion 26 and the anchor portion 28 can be formed from the same or even different materials, depending upon the desired characteristics of the tissue retention member 12. The material is of a surgical grade material, and is preferably autoclavable and reusable, though can also be disposable. In addition or alternatively, the material of tissue retention member 12 can be radiopaque, which is the relative inability of electromagnetism to pass through a particular material, particularly X-rays or similar radiation. The radiopacity of a given tissue retention member can be useful since it can allow the tissue retention member to be tracked before, during, or after a surgical procedure. Alternatively, the tissue retention member can be radiolucent, which is the relatively greater transparency of electromagnetism to pass through the material (e.g., X-rays or similar radiation). The radiolucent property of a given tissue retention member can also be useful since it can allow the tissue retention member to "disappear" and not interfere with a medical scan.

The tissue engaging portion 26 (see FIG. 4A) is configured to grasp tissue 29 surrounding an incision 30 and hold the incision 30 open, and is preferably curved, hook shaped, or otherwise bent, though can also be straight, angular, etc. In various examples, the tissue-engaging portion 26 can be hook-shaped, such as with a 5 mm or 12 mm diameter curved end that can be blunt or sharp, though various other sizes are contemplated. Alternatively, the tissue-engaging portion 26 can be a rake with one or more prongs, a clamp, a multi-prong hook, etc. It is understood that the geometry of the tissue-engaging portion 26 is not intended to limit the present invention.

The tissue retention member 12 further includes an anchor portion 28 (see FIG. 4B) coupled to the tissue-engaging portion 26 at a transition region 32. It is understood that the transition region 32 is depicted schematically in the various Figures (e.g., FIG. 3), and is emphasized for clarity. Various other examples are shown in FIGS. 5A-5D. In practice, the transition region 32 may or may not be an enlarged area, and/or may be formed as a byproduct of the coupling operation used (e.g., a welding operation, soldering, etc.). The anchor portion 28 can be removably or non-removably coupled to the tissue-engaging portion 26 in various manners. In one example, the anchor portion 28 can be non-removably coupled to the tissue-engaging portion 26 by a welding operation. For example, the anchor portion 28 can be spot welded to the tissue-engaging portion 26 to form the tissue retention member 12 prior to coupling with the elastomeric band 16. In other examples, the anchor portion 28 can be coupled to the tissue-engaging portion 26 via soldering, mechanical fasteners, adhesives, friction fits, etc. In yet another example, the anchor portion 28 can be formed together with the tissue-engaging portion 26 as a single, monolithic element. For example, the tissue retention member 12 can be formed (e.g., molded, stamped, rolled, etc.) from a single piece (e.g., single piece of wire, plate, etc.) that is worked to form each of the anchor portion 28 and the tissue-engaging portion 26, or the tissue retention member 12 can even be a single injection molded plastic element, die cast metal, etc.

Figure 5A:
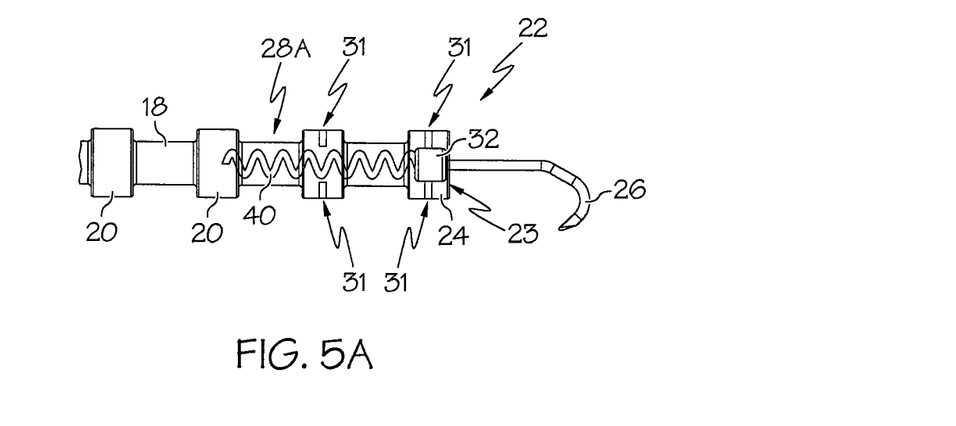
FIGS. 5A-5E are side views of various example tissue retention members embedded in the stay of detail A of FIG. 1.

The tissue retention member 12 can be coupled to the first end 22 of the band 16 such that there is not a detachable connection at the interface thereof. In one example, the anchor portion 28 can be at least partially (such as completely) embedded (such as encapsulated) within the first end 22 of the band 16. It is understood that embedded also includes the anchor portion 28 being received within a recess, hole, etc. that may be either open-ended or closed. The tissue engaging portion 26 may also be partially embedded within the first end 22, or may be completely free thereof. In any case, the tissue engaging portion 26 extends outwardly relative to (such as outwardly from) the first end 22 of the band 16. As described herein, the elastomeric band 16 is formed of a material, such as silicone rubber or urethane polymers, that inhibits disconnection of the anchor portion 28 from the band 16 during use. It is understood that various other materials can also be used to form the band 16. For example, the first end of the elastomeric band 16 can be molded about the anchor portion 28 during the formation of the band 16. As shown in FIG. 5A, one or more mold pin inserts (not shown) can be used during the molding process to maintain proper alignment of the anchor portion 28 within the first end 22 of the band 16, and such inserts can leave behind resultant mold voids 31 that have little bearing on the functionality of the stay 10 and are simply byproducts of the molding process.

The elastomeric band 16 can be formed of a material that closely conforms to the anchor portion 28 to thereby inhibit disconnection during use. For example, during the molded operation the material of the elastomeric band 16 can flow around, into, and/or through the anchor portion 28 to effectively embed the anchor portion 28 within the first end 22 of the band 16. The geometry of the anchor portion 28 can be adjusted to facilitate such close conforming action of the material, such as by providing open areas, hollow portions, apertures, through holes, projections, etc. The anchor portion 28 can extend various distances within the band 16. In one example, the anchor portion 28 can extend a distance equal to about three hubs 20. In another example, the anchor portion 28 can extend a fixed distance, such as about 5/16", 1/2" or more. It can be desirable to make the length of the anchor portion 28 relatively short to thereby reduce material costs and/or facilitate the embedding process.

Figure 5B:
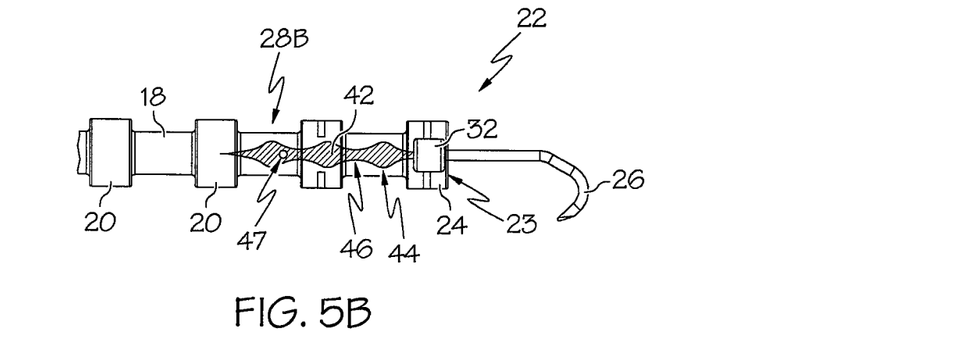
Figure 5C:
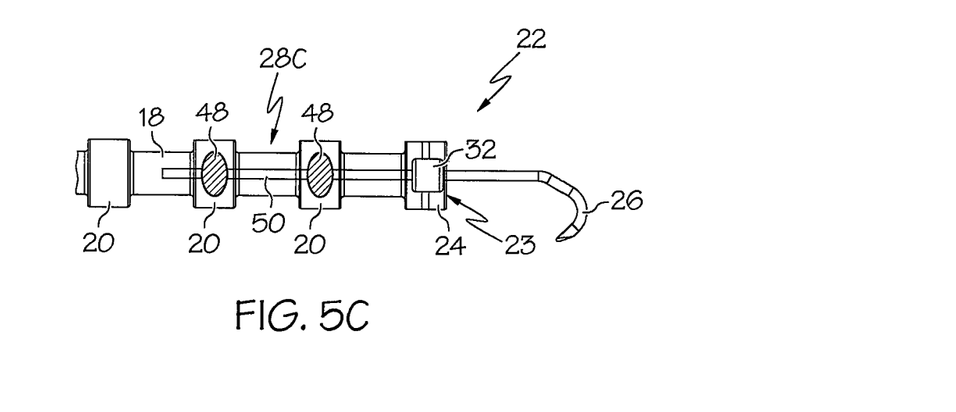
Figure 5D:
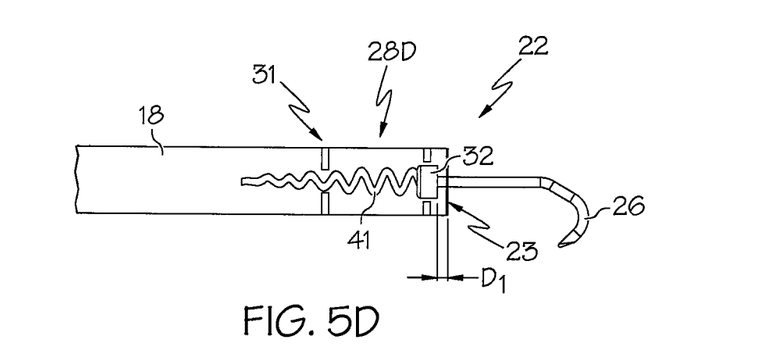

Turning now to FIGS. 5A-5D, which show detail A of FIG. 1, the anchor portion 28 of the tissue retention member 12 can include various geometries. It is understood that the shown examples are merely some of the numerous possible geometries. Various other geometries are contemplated, including combinations of the various discussed anchor portions 28, to inhibit, such as prevent, disconnection (e.g., pullout) of the anchor portion 28 from the band 16 during use. In one example, the anchor portion 28A can include a wire having plurality of bends, such as a coil 40 (see FIG. 5A). The coil 40 can have a generally cylindrical geometry with a generally hollow interior, and can have a generally constant diameter or cross-sectional dimension. For example, the generally hollow interior can permit the material of the band 16 to flow through the coil 40 to provide an increased surface area contact that inhibits disconnection (e.g., pullout) of the anchor portion 28 from the band 16 during use. Additionally, the coil 40 can be bendable about multiple axes. In other examples, the coil 40 can have a variable diameter, cross-sectional dimension, frequency, amplitude, etc. For example, as shown in FIG. 5D, the anchor portion 28D can have a modified coil 41 with an increasing or decreasing cross-sectional dimension that can provide differing amounts of flexibility, pullout strength, or tactile feel along its length. The variations in the modified coil 41 can also provide differing failure modes along its length. The coil 40, 41 can be formed of a spring material, such that the coil 40 exhibits a spring force in various axes. For example, where the coil 40, 41 is embedded in the first end 22 of the band 16, the coil 40, 41 can resiliently seek to obtain a neutral state that extends longitudinally within the elastomeric band 16. Thus, the coil 40, 41 can provide a relatively flexible and bendable feature, and when the first end 22 of the band 16 is curved or flexed (e.g., during a surgery) the coil 40, 41 can provide a resilient opposing force to facilitate holding the tissue 29.

In another example, the anchor portion 28B can include an alternating geometry 42 (see FIG. 5B). That is, the anchor portion 28B can have a geometry that changes between at least two configurations. In one example, the alternating geometry 42 of the anchor portion 28B can be a sinusoidal geometry having a generally repetitive, oscillating geometry with alternating relatively larger portions 44 and relatively smaller portions 46. The alternating relatively larger and smaller portions 44, 46 can enable the anchor portion 28B to provide an increased surface area contact that inhibits disconnection (e.g., pullout) of the anchor portion 28 from the band 16 during use. Though generally repetitive, the amplitude and/or frequency may or may not remain constant. For example, the sinusoidal geometry can include different portions having different repetitive sections. Alternatively, the geometry may not be repetitive. Additionally, the anchor portion 28B can be planar (e.g., flat plate), or twisted (e.g., helical). Further, the alternating geometry 42 may provide a relatively less flexible and bendable feature that can be useful with particular types of tissue-engaging portions 26 or tissue. In one example, the anchor portion 28B can be relatively planar to permit bending along one axis, while resisting bending in the other axes. In addition or alternatively, any of the anchor portions (e.g., 28A, 28B, 28C, etc.) can have a surface morphology or surface treatment that increases or decreases a bonding effect with the bulk material of the band 16. In various examples, the surface morphologies or surface treatments of the anchor portion 28B can include plasma coating, a porous surface, a pillar surface, etc. In another example, the anchor portion 28B can provide one or more open areas 47, such as hollow portions, apertures, through holes, etc. for receiving the bulk material of the band 16 to facilitate retention. In yet another example, the anchor portion 28 can be substantially planar having a generally standard polygonal geometry, such as square, rectangular, circular, elliptical, triangular, etc.

In yet another example, the anchor portion 28C can include a projection 48 (see FIG. 5C). That is, the anchor portion 28C can have one or more projections 48 that may be similar or different. The projection(s) 48 can extend generally outward from a central member 50 of the anchor portion 28C, which can be a central rod or the like, or can even be similar to the other anchor portions 28A or 28B. In one example, the projection(s) 48 can be a bulb, barb, wire element, or the like. The projection(s) 48 can extend outwardly at various angles, such a perpendicular to the central member 50, or at various oblique angles (e.g., an angle oriented towards or away from the first end 22). The projection(s) 48 can be disposed at various locations along the anchor portion 28C. In one example, each of the projections 48 can be arranged on the anchor portion 28 to correspond with a respective hub 20 of the band 16. The projection(s) 48 can enable the anchor portion 28C to provide an increased surface area contact via the hubs 20 that inhibits disconnection (e.g., pullout) of the anchor portion 28 from the band 16 during use. Additionally, the projections 48 can be modified to make the first end 22 relatively more or less flexible and bendable.

Figure 5E:
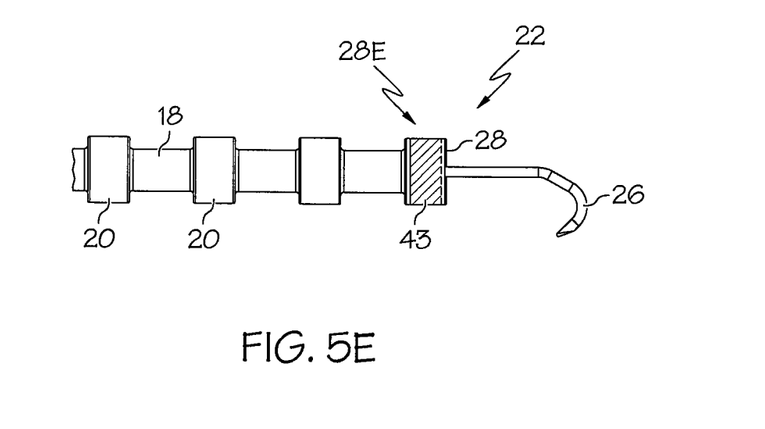

In yet other examples, the anchor portion 28 can be coupled to the first end 22 of the band 16 via mechanical fasteners, adhesives, friction fits, etc. For example, the anchor portion 28 can be glued to the first end 22 of the band 16 and/or retained due to a friction/interference fit with the first end 22. The anchor portion 28 can include surface features, treatments, etc. to facilitate such coupling. In addition or alternatively, the first end 22 can include an aperture, hole, etc. for receiving some or all of the anchor portion 28. The anchor portion 28 may or may not be embedded within the first end 22. In addition or alternatively, the anchor portion 28E can comprise an external coupler 43 (see FIG. 5E), such as a cuff, collar, or the like adapted to be placed over a portion of the first end 22, such as to receive a portion of the first end 22. The tissue engaging portion 26 can be removably or non-removably coupled to the external coupler 43. Similarly, the anchor portion 28 can be configured to be coupled to and retained on the first end 22 of the band 16 by the external coupler 43 including a retaining wire, heat shrink tubing, or the like (not shown) wrapped about the first end 22. The external coupler 43 can also act as the face of the first end 22 for engagement with the surgical frame 60. It is understood that while the external coupler 43 may or may not increase the cross-sectional dimension of the first end 22 of the band 16, substantially all of the elastomeric band (including the external coupler 43) remains configured for engagement with the surgical retractor frame 60 (and/or surgical instruments) such that the stay 10 does not include a handle. It is also understood that while described as external, portions of the external coupler 43 can removably or non-removably extend into or be received by the longitudinal body 18.

In addition or alternatively, any or all of the various anchor portions 28A, 28B, 28C can provide for differing failure modes of the stay 10 about the first end 22. That is, the anchor portion 28 and the material of the body 18 can be configured to avoid unexpected failure modes, such as silicone failure and/or coil failure (e.g., deflection). For example, varying the modulus for each of the anchor portion 28 and bulk material of the band 16 can modify (e.g., enhancing or reducing) the interfacial void formation therebetween. Depending upon the application, the modulus for each of the anchor portion 28 and bulk material of the band 16 may be substantially equal or different in order to create a seamless transfer of force and/or control failure. Generally, if the modulus of the anchor portion 28 is substantially equal to that of the bulk material of the band 16, then both components will react similarly to the overall load applied to the stay 10. However, if the modulus is different between the components, then the components will react differently. It is understood that the modulus can be Young's modulus, shear modulus, bulk modulus, etc.

For example, referring to the coil 40 of FIG. 5A, the coil's maximum deflection distance can be configured to generally coincide with the corresponding durometer's ultimate elongation of the material of the band 16. In addition, maximum force of the coil 40 (e.g., before deflection occurs) can generally coincide with the corresponding tensile strength of the durometer of the material of the band 16. Similarly, the design of the coil 40 can be chosen such that it has a k-value (e.g., spring constant) that is generally equal the modulus of the material of the band 16. These design guidelines can avoid unexpected failure modes. Of course, for other failure modes, the design of the coil 40 can be chosen such that it has a k-value (e.g., spring constant) that is different than the modulus of the material of the band 16.

In one example, the elastomeric band 16 can be formed from a material having a first modulus and the anchor portion 28 can be formed from a generally rigid material having a second modulus. As above, the first modulus can be generally equal to the second modulus to thereby avoid unexpected failure modes. In other examples, the first modulus (band 16) can be greater than the second modulus (anchor portion 28), or vice versa, such that a predetermined one of the band 16 or anchor portion 28 fails in an expected and controlled manner. For example, it is contemplated that one expected mode of failure is that the anchor portion 28 "uncoils" via a permanent, plastic deformation. In such a case, the first modulus (band 16) can be greater than the second modulus (anchor portion 28) such that the band 16 is capable of elastically deforming to a greater extent than the anchor portion 28, such that the anchor portion 28 plastically deforms first (e.g., "uncoils") while the band 16 remains elastic and generally non-deformed. The plastic deformation of the anchor portion 28 can occur relatively slowly and minimize shock forces such that the tissue-engaging portion 26 of the tissue retention member 12 does not damage the retained tissue 29.

The following design example assumes that the material of the band 16 has a durometer value of 60 D (see Table 1). The theoretical maximum load for the silicone stay 10 is about 17 lbs (e.g., 1520 psi*pi*r^2=17 lbs), where the minimum diameter of the stay 10 was used (~0.12") to determine the max load before the silicone will fail. Therefore, the coil 40 can be configured to withstand a maximum load of at least 17 lbs before deflection occurs. Additionally, the coil 40 can also be configured to withstand a minimum load above a desired engineering specification, such as 5 lbs or the like. The coil's parameters may change (e.g., coil internal diameter, wire diameter, number of coils, etc.) to achieve the similar elongation without deflection. Therefore, the coil 40 is configured to be able to elongate with the material to at least the ultimate elongation for the 60 D (450%) with k=330 psi. Still, if it is desired that the coil 40 fail before the longitudinal body 18, then the coil 40 can be adapted to withstand a maximum load less than the above-described 17 lbs. It is understood that various other values are completed, and the values discussed in this example are subject to change.

In addition or alternatively, the pullout strength of the tissue retention member 12 from the first end 22 can be modified by adjusting the insertion length and/or position of the anchor portion 28 within the first end 22 of the band 16. For example, to increase the pullout strength, the anchor portion 28 can extend a relatively greater distance into the first end 22, such as more than about ⁵⁄₁₆" or ½". In another example, to increase the pullout strength, the tissue retention member 12 can be positioned inwardly within first end 22 of the band 16 such that more of the tissue-engaging portion 26 is embedded therein. For example, as shown in FIG. 5D, relatively more of the tissue retention member 12 can be positioned within the first end 22 of the band 16 such that the transition region 32 is spaced a greater distance $D_1$ from a face 23 of the first end 22 of the band 16. Thus, a relatively greater amount of the body material (e.g., silicone, urethane, etc.) is located between the transition region 32 and the face 23 of the first end 22 to thereby increase the pullout strength of the tissue retention member 12. The distance $D_1$ between the transition region 32 and the face 23 can be adjusted to provide a desired pullout strength and/or desired failure mode. Additionally, a relatively greater amount of the body material disposed between the transition region 32 and the face 23 of the first end 22 can provide relatively more stability at the interface between the tissue-engaging portion 26 and the first end 22.

Figure 4B:
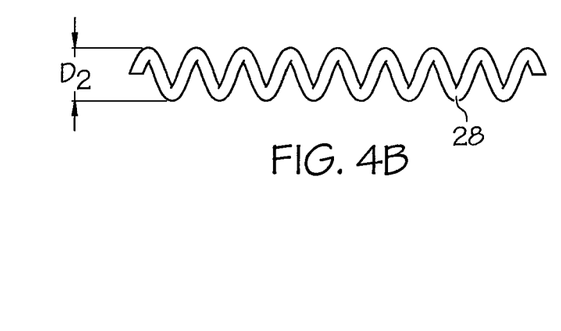
FIG. 4B is a side view of an example anchor portion of the tissue retention member of FIG. 3.

In addition or alternatively, the longitudinal body 18 of the elastomeric band 16 can include a generally uniform cross-sectional dimension with a plurality of the hubs 20 spaced at regular intervals along the length thereof. As shown in FIGS. 5A-5D, the anchor portion 28 can have a cross-sectional dimension less than the cross-sectional dimension of the longitudinal body 18 such that the anchor portion 28 can be at least partially embedded within the first end 22 of the band 16. For example, as shown in FIGS. 4B and 5A, where both of the longitudinal body 18 and coil 40 have a generally circular cross-sectional geometry, the cross-sectional diameter $D_2$ of the coil 40 can be relatively smaller than the cross-sectional diameter $D_3$ of the longitudinal body 18. Additionally, the plurality of hubs 20 can be substantially similar to thereby define a maximum cross-sectional dimension of the surgical stay 10. As shown in FIGS. 1-2, the cross-section dimension $D_4$ of the hubs 20 can be relatively larger than the cross-sectional dimension $D_3$ of the longitudinal body 18 to enable the hubs 20 to engage the retractor frame 60. For example, as shown in FIG. 5C, even though the projections 48 can be embedded within the hubs 20 and may have a relatively larger cross-sectional geometry than the longitudinal body 18, the central member 50 of the anchor portion 28C can still have a cross-sectional dimension less than the cross-sectional dimension of the longitudinal body 18. As a result, all of the longitudinal body 18 (and the hubs 20, 24, if present) are functional and the stay 10 does not include a handle of any kind. For example, each of the hubs 20, 24 can be substantially similar, define a maximum cross-sectional dimension of the surgical stay 10, and/or be spaced at regular intervals along the length of the longitudinal body 18. Similarly, although a cuff, collar, retaining wire, other mechanical fastener, etc. can be used to couple the anchor portion 28 to the first end 22, the cross-sectional diameter $D_3$ of the longitudinal body 18 and/or the cross-section dimension $D_4$ of the hubs 20 is not considered to appreciably increase, and the stay 10 is still considered to not include a handle.

As noted herein, even the hub 24 at the first end 22 of the band 16 is provided with a frame engagement surface 72 and is fully functional for engagement with the frame 60. Thus, because all of the hubs 20, 24 on the band 16 are usable with the frame 60 (and/or surgical instruments), it is understood that the stay 10 does not include a handle of any kind. That is, any portion of the stay 10 can be gripped by a user to manipulate the stay 10 as desired and no portion of the stay 10 provides a relatively greater advantage in manipulating the stay 10. Moreover, the handleless stay does not have the limitations of the conventional stay and allows more of the stay to be used for retraction. When the conventional rigid handle and the surgical frame do interact, the resultant lever action of the handle about the frame can disengage the tissue retention member(s) from the tissue. Through increased stay capacity and flexibility, a handleless stay does not exhibit such characteristic disengagement. The removal of the stay handle will allow for greater precision during placement of the stay and for placement via surgical instruments, such as hemostats and the like. These enhancements provide an increased margin of safety to the clinician and the patient due to increased visibility, control, and handling during placement. The handleless stay can also be used with surgical instruments (e.g., hemostats and the like), either together with or in place of a traditional surgical retractor frame, such as during relatively small and/or delicate surgeries (e.g., ear, nose, throat surgeries, etc.).

With additional reference to FIGS. 6-8, the stay 10 is usable with a retractor frame 60 that is adapted to surround all or part of a surgical site 62 and act as a support for the stay 10, or series of stays 10, so that the stay(s) 10 can hold the incision 30 open. It is noted that frames of this type are well known in the art and do not form part of the present invention. Example frames are discussed in U.S. Pat. Nos. 6,090,043 and 5,951,467, the entire disclosures of which are incorporated herein by reference thereto. Still, it is understood that the stay 10 can also be used with surgical instruments (e.g., hemostats and the like), either in place of or together with a traditional surgical retractor frame. In one example, the stay 10 can be used solely with surgical instruments during relatively small and/or delicate surgeries (e.g., ear, nose, throat surgeries, etc.). Accordingly, the frame 60 is only illustrated schematically and described to provide context for the present invention. The frame 60 has a flange 64 with an upper surface 66 and a lower surface 68. The upper surface 66 and the lower surface 68 are illustrated as generally planar, though can have other geometries. The frame 60 is provided with notches 70 extending from the upper surface 66 to the lower surface 68. The notches 70 are adapted to releasably receive the body 18 of the band 16. The notch 70 is preferably sized about as large as the body 18 of the band 16, sometimes smaller. Should the notch 70 be sized smaller than the body 18 of the band 16, the frame 60 will slightly compress the body 18 as it is inserted into the notch 70.

The stay 10 is used by placing the tissue engaging portion 26 of the tissue retention member 12 on the tissue 29 to be retained and inserting the body 18 of the band 16 in one of the notches 70 of the frame 60. The stay 10 is prevented from moving forward, or towards the surgical site 62, and from being pulled through the notch 70 by mechanical interference. More specifically, the hub 20 adjacent the frame 60 abuts a portion of the lower surface 68 of the frame 60 surrounding the notch 70 thereby preventing movement of the stay 10 except for stretching of the elastic band 16.

As illustrated in FIG. 7, the hubs 20 of the present invention can have an engagement surface 72 that is in contact, such as face-to-face contact, with the lower surface 68 of the frame 60. This engagement provides a distributed area where tension placed on the band 16 will be transferred to the frame 60. This distributed area is larger than, and therefore capable of absorbing greater amounts of tension, compared to a stay without hubs (not shown) or with spherical hubs (not shown), either of which can compress their way through the notch 70.

For example, the illustrated portion 74 of the engagement surface 72 that does contact the lower surface 68 can be in a flat relationship with, and make face-to-face contact with, the lower surface 68. Therefore, the forces placed on the band 16 are distributed over a broad area which is capable of absorbing relatively greater amounts of tension. When greater tension is placed on the band 16, the body 18 of the band 16 will have a tendency to be pulled further into the notch 70 and the hub 20 will have a tendency to be drawn into tighter engagement with the lower surface 68 of the frame 60, resulting in the arrangement shown in FIG. 7.

Moreover, even the hub 24 at the first end 22 of the band 16 is provided with a frame engagement surface 72 and is fully functional for engagement with the frame 60. As shown in FIG. 8, the handleless design allows for greater precision and flexibility during placement and use of the stay 10. For example, the tissue-engaging portion 26 can be used to retain tissue 29 located extremely near the retractor frame 60. The anchor portion 28 can conform to the retractor frame 60 and to the needs of the surgeon. Still, as previously discussed, the hubs 20, 24 can have various geometries that may or may not provide planar contact with the frame 60.

The above design allows for a single, universal mechanism of attachment of a functional element which interacts with biological tissue (e.g., hooks, rakes, clamps, etc. of various morphologies and purposes) to an elastic stay body. This single mechanism of attachment simplifies the manufacturing process for creating and supporting various stay types and lowers manufacturing costs. The increased number of stay types will allow for application of this new self-retaining retractor technology to an increased number of surgical procedures heretofore performed without the aid of such technology.

Various beneficial advantages are provided by the surgical stay 10 described herein. The discussion herein describes only some of the many advantages and is not intended to limit the present invention. For example, the surgical stay 10 provides a universal mechanism of attachment for various tissue retention systems, while also decreasing manufacturing costs and increasing manufacturing simplicity. The stay 10 provides a cost-effective method to expand the breadth of stay tissue retention systems for unique surgical applications. The surgical stay 10 provides increased safety for the operating room staff and surgical patient, decreased tissue damage, and increased surgical site visualization and increased operating room performance. The stay 10 also can provide for control over differing failure modes. The stay 10 reduces the resultant tissue trauma and visual obstruction caused by a rigid stay handle, which is conventional in the industry. Additionally, by removing the rigid handle portion of the stay, the elasticity/flexibility of the entire stay is increased in all or selected planes. The surgical stay 10 also provides application of self-retaining retractor system technology to an increased number of surgical procedures, as well as achieving and controlling stay elasticity/flexibility through various insert morphologies and materials, and controlling the interaction of the insert relative to the bulk material by applying various surface morphologies and bonding treatments.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. A surgical stay, comprising:
    a handleless, elastic elastomeric band comprising an elongated body having a first end and an outermost width along a substantial portion of its length, with substantially all of the elongated body having a configuration for engagement with a surgical retractor frame;
    a tissue retention member comprising a tissue engaging portion and an anchor portion, the anchor portion being at least partially embedded within the first end of the elastomeric band such that the tissue engaging portion extends outwardly relative to the first end,
    wherein the band is handleless in that the elongated body is devoid of an enlarged width portion having a width that is greater than the outermost width of the elongated body in the vicinity of the tissue retention member and anchor portion such that the entire length of the elongated body has a width that is less than or equal to the outermost width; and
    a plurality of hubs disposed along at least part of the length of the body with at least one hub being disposed adjacent the first end of the band and with each hub having a surgical retractor frame engagement surface.

2. The surgical stay of claim 1, wherein the surgical retractor frame engagement surface of each hub is generally perpendicular to a longitudinal axis of the elongated body.

3. The surgical stay of claim 1, wherein the tissue engaging portion of the tissue retention member is non-removably coupled to the anchor portion.

4. The surgical stay of claim 3, wherein the tissue engaging portion of the tissue retention member is welded to the anchor portion.

5. The surgical stay of claim 3, wherein the tissue engaging portion of the tissue retention member is formed together with the anchor portion.

6. The surgical stay of claim 1, wherein the anchor portion comprises a coil.

7. The surgical stay of claim 1, wherein the anchor portion comprises an alternating geometry.

8. The surgical stay of claim 1, wherein the anchor portion comprises a projection.

9. The surgical stay of claim 1, wherein the anchor portion comprises an external coupler.

10. The surgical stay of claim 1, wherein the anchor portion is encapsulated within the first end of the elastomeric band.

11. The surgical stay of claim 1, wherein the first end of the elastomeric band is molded about the anchor portion, the elastomeric band being formed of a material that inhibits disconnection of the anchor portion during use.

12. The surgical stay of claim 1, wherein the elastomeric band is formed from an elastomeric material having a first modulus and the anchor portion is formed from a generally rigid material having a second modulus.

13. The surgical stay of claim 12, wherein the first modulus is generally equal to the second modulus.

14. A surgical stay, comprising:
a handleless, elastic elastomeric band comprising an elongated body having a longitudinal axis and a first end and an outermost width along a substantial portion of its length, with a majority of the elongated body having a configuration for engagement with a surgical refractor frame;
a tissue retention member comprising a tissue engaging portion coupled to an anchor portion, the anchor portion being at least partially embedded within the first end of the elastomeric band such that the tissue engaging portion extends outwardly relative to the first end of the band,
wherein the band is handleless in that the elongated body is devoid of an enlarged width portion having a width that is greater than the outermost width of the elongated body in the vicinity of the tissue retention member and anchor portion such that the entire length of the elongated body has a width that is less than or equal to the outermost width; and
a plurality of hubs disposed around the body with at least one hub being disposed adjacent the first end of the band, wherein all of the plurality of hubs are adapted to make holding contact with the surgical retractor frame.

15. The surgical stay of claim 14, wherein the first end of the elastomeric band is molded about the anchor portion, the elastomeric band being formed of a material that inhibits disconnection of the anchor portion during use.

16. The surgical stay of claim 14, wherein the elastomeric band is formed from an elastomeric material having a first modulus and the anchor portion is formed from a generally rigid material having a second modulus.

17. A handleless surgical stay, comprising:
a handleless, elastic elastomeric band comprising a longitudinal body of a generally uniform cross-sectional dimension with a first end and an outermost width along a substantial portion of its length; and
a tissue retention member comprising a tissue engaging portion non-removably coupled to an anchor portion, the anchor portion having a cross-sectional dimension less than the cross-sectional dimension of the longitudinal body and being at least partially embedded within the first end of the elastomeric band such that the tissue engaging portion extends from the first end of the band and such that the uniform cross-sectional dimension of the elastomeric band is maintained when the anchor portion is embedded in the first end of the elastomeric band, the elastomeric band being formed of a material that conforms to the anchor portion to thereby inhibit disconnection during use,
wherein the band is handleless in that the elongated body is devoid of an enlarged width portion having a width that is greater than the outermost width of the elongated body in the vicinity of the tissue retention member and anchor portion such that the entire length of the elongated body has a width that is less than or equal to the outermost width, and
wherein the tissue engaging portion is non-removably coupled to the anchor portion at a transition region that is spaced a distance from a face of the first end of the band.

18. The surgical stay of claim 17, further comprising a plurality of hubs formed together with the longitudinal body and spaced at regular intervals along the longitudinal body with at least one hub being disposed adjacent the first end of the band.

19. The surgical stay of claim 18, wherein all of the hubs have a surgical retractor frame engagement surface that is substantially perpendicular to a longitudinal axis of the longitudinal body.

* * * * *